(12) United States Patent
Ferguson

(10) Patent No.: US 7,749,151 B2
(45) Date of Patent: Jul. 6, 2010

(54) BRACHYTHERAPY SPACER

(75) Inventor: Patrick J. Ferguson, Portland, OR (US)

(73) Assignee: CP Medical, Inc., Portland, OR (US)

(*) Notice: Subject to any disclaimer, the term of this patent is extended or adjusted under 35 U.S.C. 154(b) by 1247 days.

(21) Appl. No.: 11/056,037

(22) Filed: Feb. 10, 2005

(65) Prior Publication Data

US 2005/0184424 A1  Aug. 25, 2005

Related U.S. Application Data

(63) Continuation-in-part of application No. 10/328,935, filed on Dec. 23, 2002, now abandoned.

(60) Provisional application No. 60/370,140, filed on Apr. 4, 2002.

(51) Int. Cl.
*A61M 36/00* (2006.01)
(52) U.S. Cl. .......................................................... 600/7
(58) Field of Classification Search ................ 600/1–8; 606/228–231
See application file for complete search history.

(56) References Cited

U.S. PATENT DOCUMENTS

| | | | |
|---|---|---|---|
| 3,918,455 A * | 11/1975 | Coplan | 606/225 |
| 4,815,449 A | 3/1989 | Horowitz | |
| 5,242,373 A * | 9/1993 | Scott et al. | 600/7 |
| 5,626,611 A * | 5/1997 | Liu et al. | 606/230 |
| 5,713,828 A * | 2/1998 | Coniglione | 600/7 |
| 6,200,258 B1 * | 3/2001 | Slater et al. | 600/8 |
| 6,264,600 B1 * | 7/2001 | Grimm | 600/7 |
| 6,273,851 B1 * | 8/2001 | Slater et al. | 600/8 |
| 6,679,824 B1 | 1/2004 | Reed et al. | |
| 6,761,680 B2 * | 7/2004 | Terwilliger et al. | 600/8 |
| 7,118,523 B2 | 10/2006 | Loffler et al. | |
| 2005/0250973 A1 | 11/2005 | Ferguson | |

FOREIGN PATENT DOCUMENTS

| WO | WO 84/01508 | 4/1984 |
|---|---|---|
| WO | WO 00/64538 | 11/2000 |

OTHER PUBLICATIONS

File Wrapper for related and commonly owned U.S. Appl. No. 11/027,884, filed Dec. 29, 2004, Office Actions and Responses to OA's.

* cited by examiner

*Primary Examiner*—Samuel G Gilbert
(74) *Attorney, Agent, or Firm*—Silicon Forest Patent Group; Paul J. Fordenbacher, Esq

(57) ABSTRACT

System, including apparatus and methods, for positioning medical material in living tissue using hollow elements that are formed unitarily from a synthetic bioabsorbable material. The hollow elements are optionally filled with a core material and a heat shrink process is performed so that the hollow elements are tightened around the core material.

26 Claims, 2 Drawing Sheets

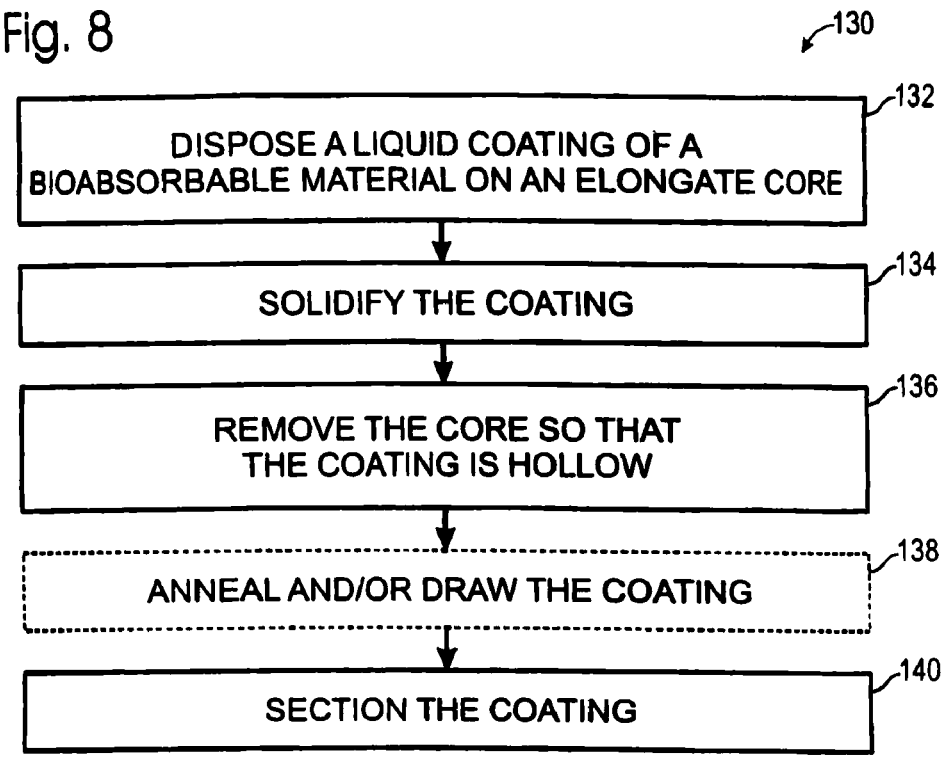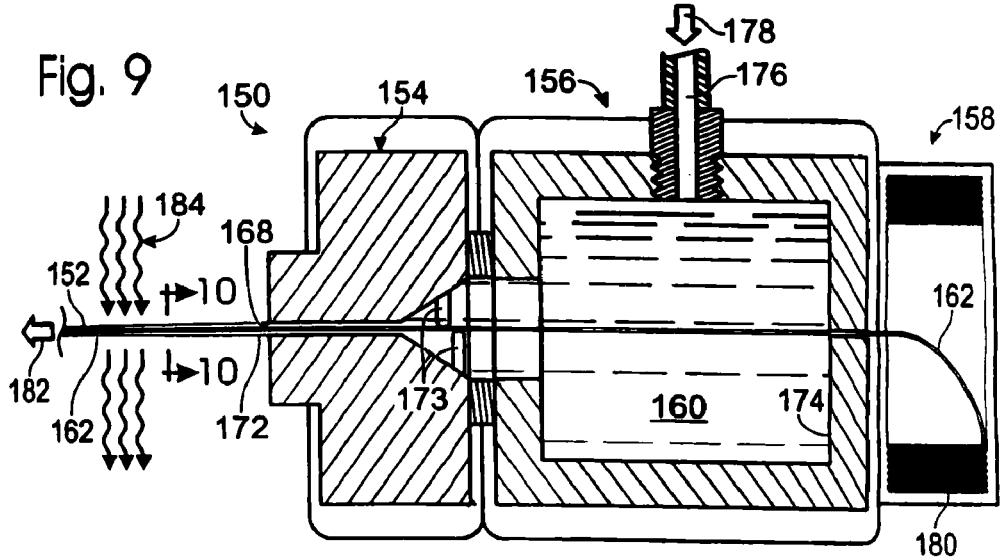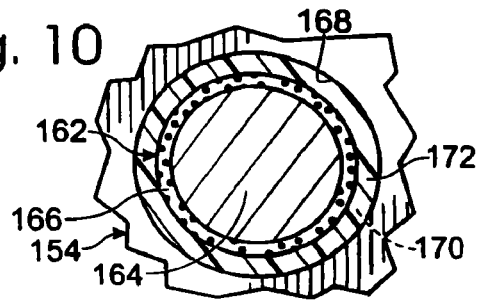

BRACHYTHERAPY SPACER

CROSS-REFERENCES

This application is a Continuation-In-Part of U.S. Ser. No. 10/328,935, filed on Dec. 23, 2002, now abandoned which claims priority under 35 U.S.C. § 119 from U.S. Provisional Patent Application Ser. No. 60/370,140, filed Apr. 4, 2002.

FIELD OF THE INVENTION

The invention relates to positioning material in living tissue. More particularly, the invention relates to positioning medical material, such as radioactive seeds or therapeutic drugs, in living tissue using hollow, bioabsorbable elements that are formed unitarily from synthetic material.

BACKGROUND

Some medical treatments rely on implanting a medical material, such as a time-released drug or a radiation source, at a target site within a patient to direct localized action. For example, brachytherapy is a form of internal radiation therapy in which radioactive materials are introduced near or within a tumor of a cancer patient. Such radioactive materials may provide a high dose rate (HDR) treatment during transient implantation, and then may be removed. Alternatively, low dose-rate (LDR) materials may be implanted more permanently in the cancer patient and allowed to decay radioactively over a longer time period.

LDR brachytherapy is used commonly for treating prostrate cancer. In such LDR treatment, radioactive "seeds" act as radiation sources implanted at predefined regions within (or near) a prostate tumor, directing a sustained, localized dose of radiation to the tumor, with reduced radiation exposure to surrounding healthy tissue.

Cannula/stylet assemblies are utilized to deliver the radioactive seeds to tumors during LDR brachytherapy. A cannula (or needle) having a central bore receives the seeds in the bore, and a distal end of the cannula is inserted into a tumor. The cannula also receives a stylet in the central bore at a proximal end of the cannula. The seeds are implanted in the tumor by retracting the proximal end of the cannula over the stylet. This process ejects the seeds from the distal end of the cannula along a path in the tumor defined by the distal end as it is pull through the tumor. Alternatively, the seeds may be placed within or near the tumor using other techniques, for example, during surgery.

The seeds may be positioned more precisely and stably in the tumor by arraying the seeds beforehand using positioning elements. One such positioning element, termed a carrier, may be disposed around the seeds, to enclose or encapsulate a set of the seeds. The carrier may prevent seeds from migrating away from their sites of delivery within a tumor, thus reducing undesired exposure of adjacent healthy tissue. Alternatively, or in addition, other positioning elements, termed spacers, may be disposed between seeds to define the spacing between adjacent seeds or from the end of a carrier. Accordingly, spacers may be useful to distribute a radiation dose more uniformly and precisely within the tumor.

Since carriers and spacers are not removed manually after delivery to tissue, they may be configured beneficially to be bioabsorbable. In particular, their rate of bioabsorption may be a least several-fold longer than the effective lifetime of the radioactive seeds, so that the carriers and spacers continue to position the seeds until the seeds are no longer providing a therapeutic dose of radiation. Bioabsorbable materials used to produce carriers and spacer may be natural or synthetic.

Natural materials, such as catgut, have been used to form bioabsorbable carriers. However, these materials may be inadequate for a number of reasons. For example, such natural materials may be difficult to adapt to manufacturing processes, resulting in carriers with non-uniform shapes and/or inconsistent diameters. In addition, many natural materials are fibrous and thus the carriers may fray. As a result, these carriers may not travel smoothly within the cannula during loading and ejection, and thus may compromise seed implantation and subsequent tumor irradiation. Furthermore, carriers formed of natural materials may be difficult to sterilize and may carry impurities with unwanted biological activities.

Synthetic materials also have been used to form carriers, as an assembly of fibers (see FIG. 1). The assembly forms a tube 20 from a plurality of thin, solid fibers 22 that are braided or woven in a tubular configuration around a removable core 24. Tube 20 generally is flexible and expandable as manufactured, but, with heating, the tube can be rigidified. However, such multi-fiber carriers suffer from some of the same problems associated with carriers formed of natural materials. For example, they may tend to stick within a cannula because they have a varying diameter, lack a smooth exterior surface, and/or have a tendency to fray.

SUMMARY OF THE INVENTION

The invention provides a system, including apparatus and methods, for positioning medical material in living tissue using hollow elements that are formed unitarily from a synthetic bioabsorbable material.

BRIEF DESCRIPTION OF THE DRAWINGS

FIG. 8 is a flowchart showing an embodiment of a method for unitarily forming hollow positioning elements from synthetic bioabsorbable material.

FIG. 9 is a sectional view of an embodiment of a system for forming a monofilament sheath that can removed from its core and segmented to provide the positioning element of FIG. 4.

FIG. 10 is a fragmentary sectional view of the system of FIG. 9, taken generally along line 10-10 of FIG. 9.

DETAILED DESCRIPTION

The invention provides a system, including apparatus and methods, for positioning medical material in living tissue using hollow elements that are formed unitarily from a synthetic bioabsorbable material. In some embodiments, the hollow elements may be used as bioabsorbable carriers and/or spacers for implanting radioactive seeds. A carrier and/or one or more spacers may be combined with one or more seeds to form a seed assembly for delivering the seed(s) into tissue. Each seed carrier may provide an elongate sleeve within which one or more radioactive seeds (or other medical materials) are retained. The seed spacers may separate the seeds so that the seeds are disposed in a spaced array, for example, within a carrier. In some embodiments, the seed assembly includes a hollow carrier and hollow spacers, each formed unitarily from the same synthetic bioabsorbable material.

The methods may include processes for unitarily forming hollow bioabsorbable monofilaments from which the positioning elements can be fabricated. In some embodiments, the processes may produce each monofilament as a coating of synthetic bioabsorbable material on an elongate core. Removal of the core creates the hollow monofilament, which may be segmented into positioning elements of any suitable length.

Figure 2:
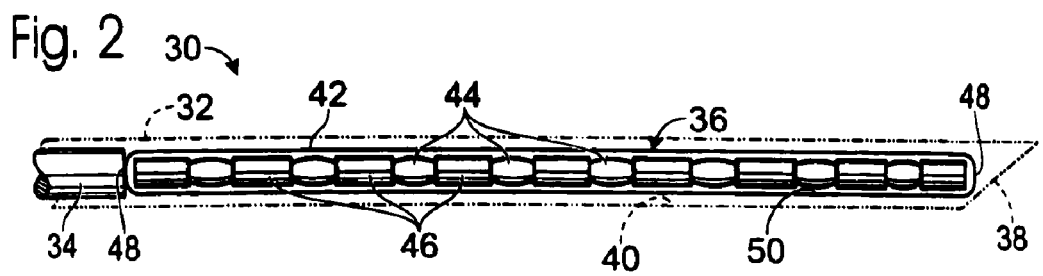
FIG. 2 is an embodiment of a system for introducing material into living tissue using a cannula and a stylet, with the cannula holding an array of radioactive seeds enclosed by a carrier and separated by spacers.

FIG. 2 shows an embodiment of a system 30 for positioning medical material in living tissue. System 30 may include a cannula or needle 32, a stylet 34, and a seed assembly 36. Cannula 32 may include a pointed distal end 38 at which the cannula can be directed into tissue. Both stylet 34 and seed assembly 36 may be configured to be received by, and slidable within, bore 40 of the cannula. The stylet may be configured as a rod that is movable reciprocally within the bore of the cannula. Accordingly, relative advancement of the stylet from the proximal end of the cannula toward distal end 38 may be used to deliver pre-loaded seed assembly 36 as a unit from the distal end into tissue. As used herein, "positioning in tissue" means facilitating establishment and/or maintenance of position within an organism in tissue or near tissue, for example, in a cavity adjacent to tissue.

Figure 3:
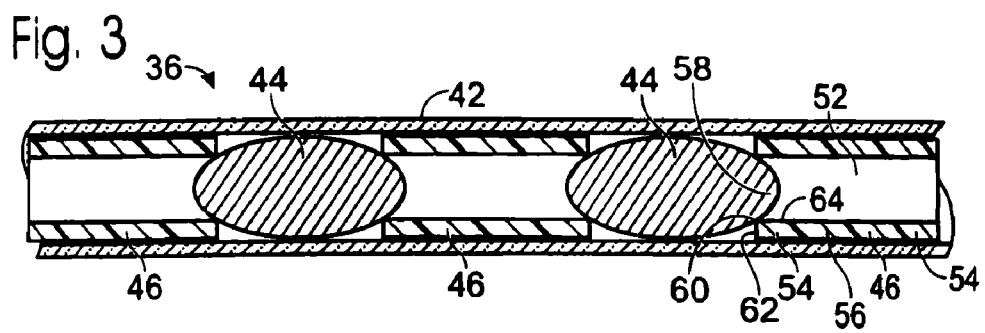
FIG. 3 is a fragmentary sectional view of the seed array, carrier, and spacers of FIG. 2.

FIGS. 2 and 3 show how positioning elements may be used in seed assembly 36. Seed assembly 36 may include a carrier 42 that substantially or completely encloses one or more seeds 44 (or other medical material). Alternatively, or in addition, the assembly may include one or more spacers 46 disposed between and/or flanking the seeds.

Carrier 42 may be configured to receive and retain seeds 44 and spacer 46. Accordingly, the carrier may have an inner diameter that is greater than the outer diameter of the seeds and spacers. Carrier 42 may have end regions 48 configured to retain material within a cavity 50 of the carrier. For example, the end regions may be deformed (for example, crimped toward the central axis after heating, solvent treatment, etc.), plugged, swelled, or the like to prevent seeds 44 and spacers 46 from falling out end regions 48. Alternatively, the outer diameter of the seeds or spacers may correspond closely to the inner diameter of the carrier to retain the seeds and spacers by friction.

Seeds 44 may have any suitable shape, size, structure, and radionuclide content according to their intended delivery mechanism and purpose within tissue. The seeds may have any suitable shape including ellipsoidal as shown, cylindrical, spherical, etc. In some embodiments, the seeds may have protrusions of reduced diameter that extend from one or both ends, for example, formed by swaged ends. The seeds may have any suitable size, but are generally sized to be slidable within cavity 50 of the carrier and/or bore 40 of cannula 32. The seeds may include a casing, such as metal, plastic, a bioabsorbable material, or the like, which may enclose any suitable radionuclide or mixture, such as iodine-125, iridium-192, or palladium-103, among others. Alternatively, or in addition, carrier 42 may include any other suitable medical material in any suitable form. As used herein, "medical material" includes any material introduced into a person or other animal for any therapeutic, diagnostic, and/or prognostic purpose. Exemplary medical materials may include a drug, a sensor (mechanical, optical, acoustic, electrical, etc.), a test reagent, or a radioactive implant (or seed), among others.

Spacers 46 may have any suitable shape and size. Here, the spacers are generally tubular, with a hollow core 52 extending from end regions 54 through central region 56 (see FIG. 3). However, in some embodiments the spacers may have other shapes, may be solid rather than hollow, and/or may be hollow at end regions 54 but solid at central region 56. Alternatively, the spacers may be hollow at central region 56 but partially or completely closed at end regions 54, for example, by sealing, crimping, or plugging the end regions. Spacer 46 may be sized to be slidably received within the cavity of carrier 42. Alternatively, the spacer may be used to position seeds in the absence of a carrier.

Spacer 46 may have an inner diameter (defined by core 52) configured to receive an end portion 58 of seed 44. Contact between end portion 58 of the seed and end region 54 of the spacer may define how far the seed enters core 52. Such contact may be between end portion 58 and inner edge 60 (as shown), end surface 62, or inner surface 64, based on the size and shape of seed 44. Contact with end surface 62 may limit travel of the seed into the spacer when the seed has a widened shoulder region flanking a narrowed protrusion at the end of the seed, or when the seed has a flat or concave end. Contact with inner surface 64 may limit travel, for example, when the seed is sized to fit frictionally in core 52.

Figure 1:
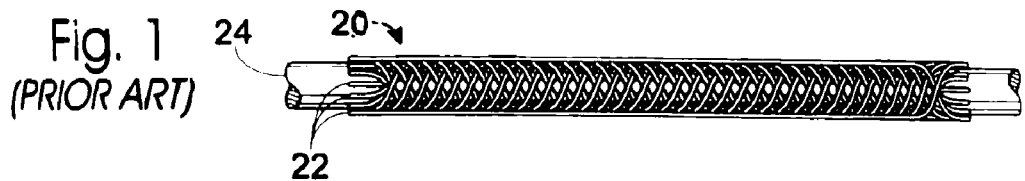
FIG. 1 is a side elevation view of an embodiment of a synthetic bioabsorbable tube from the prior art, with the tube formed from multiple solid fibers braided around a central core.
Figure 4:
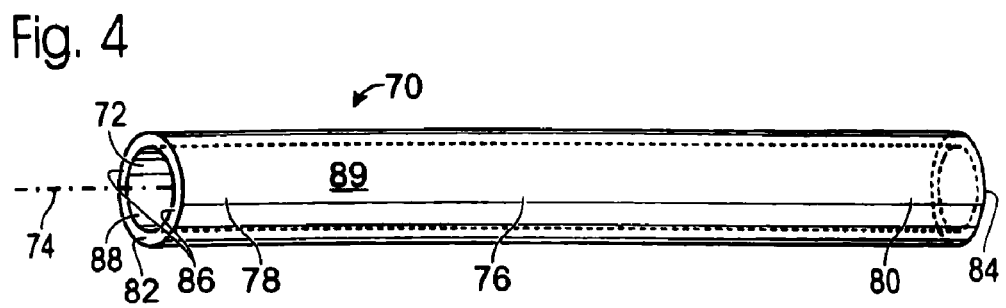
FIG. 4 is a view of a hollow positioning element formed unitarily from a synthetic bioabsorbable material, in accordance with aspects of the invention.

FIG. 4 shows an embodiment of a hollow, bioabsorbable positioning element 70 that may be used, for example, as carrier 42 or spacer 46. Positioning element 70 is unitary, that is, formed unitarily or as a single piece from a synthetic material, rather than from a multi-component assembly, such as that shown in FIG. 1. Positioning element 70 may include a hollow core or central cavity 72 that extends parallel to central axis 74, from central region 76 to end regions 78, 80. In some embodiments, for example, when the end regions are not sealed, central cavity 72 may extend to opposing end surfaces 82, 84. In still other embodiments, central cavity 72 is filled with a material such as a suture material. Element 70 has side walls 86 that may surround and enclose cavity 72 parallel to central axis 74, that is, along the length of the element. Side walls 86 may provide an inner surface 88 and an outer surface 89, each of which may be substantially smoother and more even than the inner and outer surfaces of positioning elements formed from multi-fiber tubing.

Figure 5:
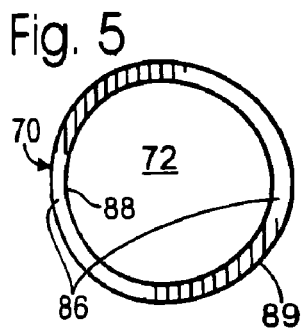
FIG. 5 is an end view of the positioning element of FIG. 4.

Positioning element 70 may have any suitable shape. Positioning element may be generally cylindrical or tubular, thus being circular in end view, as defined by inner surface 88 and outer surface 89, and as shown in FIGS. 4 and 5. Alternatively, positioning element 70 may have any other shape including cross-sectional shapes that are elliptical, polygonal (square, triangular, hexagonal, etc.), and/or a combination thereof, among others, as defined by the inner and/or outer surfaces. In some embodiments, the positioning element may be seamless. Opposing end surfaces 82, 84 may extend generally normal to central axis 74, as shown in FIG. 4, or may extend obliquely, or be crimped or flared.

Figure 6:
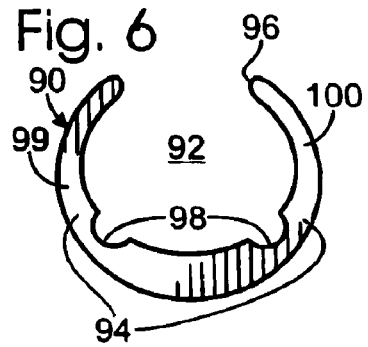
FIG. 6 is an end view of an embodiment of a hollow positioning element that has an opening in its side walls.
Figure 7:
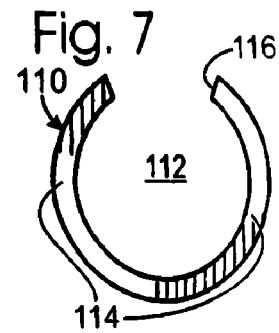
FIG. 7 is an end view of an alternative embodiment of a hollow positioning element that has an opening in its side walls.

Side walls 86 may have a uniform thickness, as shown in the end view of FIG. 5. Alternatively, side walls 86 may have a nonuniform thickness that varies angularly around the central axis of the element. For example, FIGS. 6 and 7 show positioning elements with a gap or opening in the side walls. FIG. 6 shows positioning element 90 with an asymmetrically disposed cavity 92 and side walls 94 that may generally taper toward an opening 96 in the side walls. Accordingly, side walls 94 may be thickest at positions generally opposing opening 96. Side walls 94 may include one or more interior (or exterior) grooves 98 that extend longitudinally, generally parallel to opening 96. The grooves may act, for example, as hinge sites of increased flexibility for changing the spacing between opposing side wall regions 99, 100. Opening 96 and cavity 92 together may define a channel that extends partially or completely between opposing ends of element 90. FIG. 7 shows positioning element 110 with a centrally disposed cavity 112 and side walls 114 of substantially uniform thickness that define a longitudinal opening 116. Opening 116, like opening 96 described above, may extend partially or completely between opposing ends of the element.

Positioning elements may have any suitable outer and inner diameters and wall thickness based on intended use. Outer diameters may be less than about 5 mm, inner diameters less than about 4 mm, and the wall thickness less than about 2 mm. In some embodiments, the positioning element is configured to be received by a cavity with an inner diameter, such as the cavity or bore defined by a cannula (needle) or a carrier. Accordingly the outer diameter of the element may be less than the inner diameter of such a cavity or bore. In some embodiments, suitable needle gauges for delivering a seed assembly may be a gauge of 12 to 22, with an approximate bore diameter of 0.5 to 2 mm, or about 18 gauge with a bore diameter of about 1 mm. For use as a carrier in an 18-gauge needle, the positioning element may have an exemplary outer diameter of about 0.8 mm and a wall thickness of about 0.05 mm. When the positioning element is configured for use as a spacer, the positioning element may have an outer diameter less than the inner bore of a needle, as described above. In addition, the positioning element may have an outer diameter less than the inner diameter of a carrier, so that the positioning element can be slidably disposed within the carrier.

A positioning element may have any suitable length based on the intended use of the element. In some embodiments, the positioning element is elongate. When used as a seed carrier, the positioning element may have a length suitable to carry an appropriate number of seeds, and, optionally, spacers. When used as a spacer, the positioning element may have a length generally corresponding to the desired spacing between seeds (or other medical materials). Accordingly, the spacer length may be less than, substantially the same as, or more than the length of a seed.

A positioning element may be formed of or include a synthetic bioabsorbable material. As used herein, "synthetic" means that a majority of the material was produced artificially in its final chemical form. As used herein, "bioabsorbable" means that the material is substantially solubilized and/or broken down into smaller components over time within the body, generally so that the material can be excreted or metabolized. The material may be broken down by any suitable enzymatic or chemical reactions. In some embodiments, the material is broken down substantially by hydrolysis. Bioabsorption may be completed over a period of hours, days, weeks, months, or years, according to the specific formulation and processing of the bioabsorbable material before introduction into tissue. The synthetic bioabsorbable material may be rigid enough that the positioning element retains its cross-sectional shape and cavity shape with normal handling, but flexible enough to flex somewhat or even be coiled along its length.

The bioabsorbable material may be a polymer. Suitable polymers may be linear polymers, and may include polyesters, such as polyglycolic acid (PGA), polylactic acid (PLA; D-form, L-form, or a D,L mixture), polydioxanone, polycaprolactone, polyhydroxybutyrate, copolymers thereof, or mixtures thereof, among others. In some embodiments, the bioabsorbable material includes 70-100% PGA and 0-30% PLA. In an exemplary embodiment, the bioabsorbable material is a 90:10 copolymer of PGA:PLA, available as POLYGLACTIN 910 from Ethicon, Inc. In other embodiments, the bioabsorbable material includes 0-30% PGA and 70-100% PLA. In a second embodiment, the bioabsorbable material is a 20:80 copolymer of PGA:PLA, available from Ethicon, Inc., US Surgical, Alkermes or Purac. A suitable polymer may melt to a liquid form at elevated temperature and solidify at room temperature.

FIG. 8 shows an embodiment of a method 130 for unitarily forming synthetic, bioabsorbable positioning elements that are hollow. Method 130 also may provide a hollow, bioabsorbable monofilament that may be used to fabricate the positioning elements.

In method 130, a liquid coating of a bioabsorbable material may be disposed on an elongate core, shown at 132. The bioabsorbable material may be liquefied, for example, by heating the material above its melting point. The bioabsorbable material may be any of the synthetic bioabsorbable materials described above. In an exemplary embodiment, POLYGLACTIN 910 is heated to about 210-220° C. In a second embodiment, the 20:80 copolymer of PGA:PLA is heated to about 190-210° C.

The coating may be disposed by any suitable method. For example, the coating may be disposed by dipping the core in the bioabsorbable material (dip coating) or by passing the core through a die in the presence of the bioabsorbable material. When using a die, the die may include an aperture with a diameter greater than the outer diameter of the elongate core, so that the space between the core and the aperture generally defines the thickness of the coating (and the inner and outer cross-sectional shapes). The die also may include centering features, such as adjustable centering screws, that position the core centrally (or asymmetrically) within the aperture. Such centering features may be used to provide a uniform or non-uniform wall thickness (compare FIGS. 5 and 6), based on the position of the core within the aperture. In some embodiments, the die may include a blade (or blades) that cut an opening, such as opening 116 (see FIG. 7). Alternatively, the space defined between the core and the die may not extend completely around the core, so that an opening, such as opening 96 of FIG. 6, is created as the coating is disposed on the core.

The elongate core may have any suitable shape and size. The cross-sectional shape of the core may define the cross-sectional shape of inner surface 82 (see FIG. 4), so the core may be cylindrical, with a circular cross section, or have an elliptical, polygonal, or other cross-sectional shape. In some embodiments, the core may include longitudinally extending ridges (or grooves) to form corresponding grooves (or ridges) on the coating (for example, see grooves 98 of FIG. 6). The diameter of the core may define the inner diameter of the coating, thus a suitable core diameter may be selected based on the desired inner diameter of the coating in conjunction with any reduction in diameter to be produced by drawing down the coating (see below). The core may have a length at least as long as the coating to be formed on the core or substantially longer.

The core may have any structure and composition. The core may be a single component or may have a central core portion with a layer or coating surrounding and attached to the central core portion. The core or central core portion may be formed of metal, plastic, glass, ceramic, and/or the like. In some embodiments, the core has a central core portion defined by a metal wire (such as copper or stainless steel) and a polymer layer that coats the metal wire. The wire may be a single strand. Alternatively, the wire may be a braided assembly of multiple strands, for example, to increase the elasticity of the wire (see below).

After the coating is disposed on the core, the coating may be solidified, as shown at 134. Suitable solidification procedures are determined by the properties of the bioabsorbable material used. In some embodiments, solidification may be conducted by cooling the coating below its melting temperature, for example, by contact with air or placing the coating in a water bath. Alternatively, solidification may be conducted or promoted by heat, light (any electromagnetic radiation), pressure, etc.

The core then may be removed to provide a hollow coating or monofilament, shown at 136. Generally, the core slides out from the coating (or the coating off of the core) by providing appropriate axially directed forces on the core and coating. To promote such sliding, the core may have a smooth exterior surface that does not adhere to the inner surface of the coating. Suitable exterior surfaces may be provided by a polymer, metal, glass, ceramic, or the like. In some embodiments, the polymer may be a poly(fluorocarbon), such as polytetrafluoroethylene (TEFLON), or PDSlick, which is polyimide tubing available from Phelps Dodge High Performance Conductors. The polymer is provided by a distinct layer disposed on a central portion of the core or forming the entire core. In some embodiments, the central portion of the core has a roughened surface to promote frictional contact with a nonadherent layer disposed on the roughened surface. For example, the central portion may be a wire that has an etched surface (for example, etched with acid) upon which a polymeric fluorocarbon or other suitable nonadherent material is disposed. Such a nonadherent layer may be disposed on the central core portion generally as described above for step 132. Removing the core from the coating also may be promoted with an elastic core, for example, formed of braided wire, so that axial stretching reduces the diameter of the core and promotes its removal from the coating.

The solidified coating optionally may be annealed and/or drawn at any time, shown at 138. Accordingly, annealing and/or drawings may be carried out before or after removing the core and before or after sectioning the coating (see below). Annealing may be conducted, for example, by heating the solidified coating, and may improve dimensional or chemical stability, among others. Drawing stretches the coating axially and may be used, for example, to improve dimensional stability or to reduce the diameter of the coating. Any drawdown ratio may be used.

The solidified coating or hollow monofilament may be sectioned (or segmented) to form positioning elements, shown at 140. Sectioning may be carried out by cutting the coating before and/or after removing the elongate core from the coating. In an exemplary embodiment, the coated core is sectioned to about 1-2 meter lengths, the core removed, and then the hollow coating further sectioned. The coating or monofilament may be cut to any desired length based on the type of positioning element produced. Sectioning may be normal or oblique to the central (long) axis of the coating or monofilament.

EXAMPLE 1

In a first example, the bioabsorbable material is a 90:10 copolymer of PGA:PLA available as POLYGLACTIN 910 from Ethicon, Inc. The POLYGLACTIN 910 is liquefied by heating to about 210-220° C. The liquefied material is then disposed on an elongate core. The elongate core includes a central core and a layer of TEFLON surrounding the core. After solidification, the bioabsorbable material is removed from the core, thus providing a hollow monofilament. The hollow monofilament produced in this example has an absorption time of 60-90 days.

EXAMPLE 2

In a second example, the bioabsorbable material is a 20:80 copolymer of PGA:PLA available from Ethicon, Inc., US Surgical, Alkermes or Purac. The bioabsorbable material is liquefied by heating to about 190-210° C. The liquefied material is then disposed on an elongate core. The elongate core includes a central core and a layer of PDSlick surrounding the core. A coating of PDSlick is preferable to TEFLON in this example since the bioabsorbable material formed in this example is much stickier than the formulation in example 1 and will stick to TEFLON. After solidification, the bioabsorbable material is removed from the core, thus providing a hollow monofilament. The hollow monofilament is sterilized by irradiation. The hollow monofilament produced in this example has an absorption time of 6-9 months.

As shown in the above examples, variations in the formulations and methods for producing the monofilament of the present invention produce vastly different absorption times. Thus, the formulation and the method can be adjusted to achieve a desired absorption time.

FIGS. 9 and 10 show an embodiment of a system 150 for forming a monofilament sheath 152 that can be segmented to provide, for example, positioning element 70 of FIG. 4. System 150 may include a die 154 configured to shape an outer surface of sheath 152. System 150 also may include a fluid supply mechanism 156 and a core conveyance mechanism 158, configured to feed a fluid bioabsorbable material 160 and an elongate core 162, respectively, to die 154. Core 162 may include a central core 164 and a nonadherent sheath 166, such as a poly(fluorocarbon) layer, disposed around the central core.

Die 154 may have any suitable structure that positions bioabsorbable material 160 and core 162 in the desired spatial arrangement as they exit the die together. Accordingly, the die may include an aperture or orifice 168 through which bioabsorbable material 160 and core 162 are extruded. FIG. 10 shows that orifice 168 may have a diameter that is larger than core 162, providing a space 170 between the core and the orifice at which a coating 172 is disposed on core 162. Die 154 also may include alignment elements 173 that position core 162 centrally or asymmetrically within orifice 168.

Fluid supply mechanism 156 may include any suitable mechanisms to contain, liquefy, mix, move, filter, and/or monitor bioabsorbable material 160. Containing or holding mechanisms may include one or more fluid chambers, such as chamber 174, in which the bioabsorbable material is stored during operation of system 150. Liquefying mechanisms may include a heater that melts a solid form of the bioabsorbable material and maintains the material as liquefied. The liquefying mechanisms may be included in fluid chamber 174 and/or in other separate storage chambers that feed fluid chamber 174. Mixers may be included to introduce additives to bioabsorbable material 160, to prevent separation of components, to facilitate heat distribution, and/or the like. Bioabsorbable material 160 may be moved within fluid supply mechanism 156 toward, for example, die 154 or from a storage chamber to fluid chamber 174 along supply conduit 176, shown at 178. Fluid may be moved by pressure, such as exerted by a mechanical pump and/or by pressurized gas, among others. Water introduced into liquid bioabsorbable material may promote hydrolytic breakdown. Accordingly, an anhydrous gas, such as dry nitrogen or air, or a hygroscopic agent also may be used to reduce the amount of water that enters system 150. Fluid supply mechanism 156 also may include a filter that removes particulates from bioabsorbable material 160. Properties of bioabsorbable material 160, such as temperature, flow rate, presence/absence, or optical absorbance, among others, may be monitored with suitable sensors.

Core conveyance mechanism 158 may include any mechanism that moves core 162 through die 154, by pushing and/or pulling the core. Here, conveyance mechanism 158 includes a deployment mechanism that includes a spool 180. Spool 180 stores core 162 and feeds core toward die 154 at a desired rate. Conveyance mechanism also may include a puller that pulls core 162, shown at 182, through die 154. The conveyance mechanism may bring core 162 and its new coating 172 past or through a solidification mechanism 184, which may cool coating 172 to facilitate solidification of the coating.

Solidification of coating 172 forms monofilament sheath 152. Sheath 152 may be further processed while disposed on core 162 or after separation of the sheath from the core. Such processing may include annealing, drawing, and/or sectioning, as described above for method 130 of FIG. 8.

Attempts have been made in the prior art to use suture material, such as Rapid Strand manufactured by Boston Scientific, as spacers. A problem with using suture material as spacers is that the suture material begins to unravel and loses its shape, thus swelling in the cannula. As a result, these spacers may not travel smoothly within the cannula during loading and ejection, and thus may compromise seed implantation and subsequent tumor irradiation.

In order to use suture material as spacers, the monofilament sheath of the present invention is used to form a cover around the suture material, thus maintaining the size and shape of the small section of suture material. In this embodiment, the monofilament sheath has an opening in the sidewall, such as those in FIGS. 6 and 7. The sheath may be made by any of the methods discussed above and be made of any of the materials discussed above. After forming the hollow sheath, the suture material is inserted through the opening in the sidewall. The suture material is preferably bioabsorbable, such as Rapid Strand available from Boston Scientific. Then, a heat shrink process is performed so that the sheath tightens around the suture core. The sheath with a suture core may then be cut to form spacers of any desired size.

The steps of the above process may be performed in a different order. For example, the cutting step could be performed before the heat shrinking step or before the step of filling the sheath with the suture material.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

I claim:

1. A positioning element produced according to the method comprising:
   forming a hollow sheath, wherein the sheath comprises a cavity surrounded by a sidewall formed of a synthetic bioabsorbable material, the sheath having an opening in the sidewall;
   filling the cavity of the sheath with a suture material;
   performing a heat shrink process; and
   cutting the sheath into a plurality of segments.

2. A device for spacing medical materials in tissue, comprising:
   a tubular sheath having a sidewall defining a cavity, the sidewall defining an opening along a length of the tubular sheath, the tubular sheath configured to be disposed between a pair of the medical materials to define a spacing between the pair of the medical materials, the tubular sheath being formed unitarily of a synthetic bioabsorbable material; and
   a core material disposed within the tubular sheath.

3. The device of claim 2, wherein the sheath and the medical materials are configured to be received in a cannula for delivery into the tissue.

4. The device of claim 2, the sheath being configured to be disposed in a carrier that holds the sheath and medical materials during delivery from a cannula into the tissue.

5. The device of claim 2, wherein the core material comprises suture material.

6. The device of claim 2, wherein the medical materials are radioactive seeds.

7. The device of claim 2, wherein the synthetic bioabsorbable material includes a polymer, the polymer including as least one of polyglycolic acid, polylactic acid, and polydioxanone.

8. The device of claim 2, wherein the sheath comprises a first end and a second end opposite the first end, wherein the sidewall defines at least one groove adjacent the cavity, the at least one groove extending longitudinally from about the first end to about the second end.

9. The device of claim 2, wherein the sheath comprises a first end and a second end opposite the first end, wherein the sidewall defines at least one groove adjacent the cavity, the at least one groove extending longitudinally from a first end to a second end.

10. A system for spacing medical materials in tissue comprising:
    a hollow cannula;
    a plurality of medical materials disposed within the cannula; and
    spacers disposed within the cannula and between the medical materials, wherein each spacer comprises a filler material surrounded by a sheath, the sheath comprising a sheath sidewall, the sheath sidewall defining a tubular-shaped sheath cavity, the sheath sidewall having an opening in the sheath sidewall.

11. The system of claim 10, wherein the filler material is a suture material.

12. The system of claim 10, wherein the sheath is made of a synthetic bioabsorbable material.

13. The system of claim 12, wherein the medical materials and the spacers are disposed in a carrier and the carrier is disposed in the cannula.

14. The system of claim 13, wherein the carrier is made of the synthetic bioabsorbable material.

15. The system of claim 14, wherein the carrier comprises a carrier sidewall defining a tubular-shaped carrier cavity, the carrier sidewall defining an opening along a length of the carrier.

16. The system of claim 15, wherein the carrier cavity defines at least one groove in the carrier sidewall.

17. The system of claim 16, wherein the carrier comprises a carrier first end and a carrier second end opposite the carrier first end, wherein the carrier sidewall defines at least one groove adjacent the carrier cavity, the at least one groove extending longitudinally from about the carrier first end to about the carrier second end.

18. The system of claim 16, wherein the carrier comprises a carrier first end and a carrier second end opposite the carrier first end, wherein the carrier sidewall defines at least one groove adjacent the carrier cavity, the at least one groove extending longitudinally from the carrier first end to the carrier second end.

19. The system of claim 10, wherein the medical materials are radioactive seeds.

20. The system of claim 10, wherein the synthetic bioabsorbable material includes a polymer, the polymer including as least one of polyglycolic acid, polylactic acid, and polydioxanone.

21. An apparatus, comprising:
a tubular-shaped sheath having a first end and a second end opposite the first end, the tubular sheath having a sidewall defining a cavity, the sidewall defining an opening along a length of the tubular sheath, the tubular sheath operable to be disposed between a pair of the medical materials to define a space between the pair of the medical materials; and
a core material disposed within the cavity.

22. The device of claim 21, wherein the sidewall defines at least one groove adjacent the cavity, the at least one groove extending from about the first end to about the second end.

23. The device of claim 21, wherein the sidewall defines at least one groove adjacent the cavity, the at least one groove extending from the first end to the second end.

24. The device of claim 21, wherein the sidewall has a tapered thickness that is thickest at a position generally opposing the opening.

25. The apparatus of claim 21, wherein the core material comprises suture material.

26. The apparatus of claim 21, wherein the sheath comprises a bioabsorbable material.

\* \* \* \* \*